(12) United States Patent
Koka et al.

(10) Patent No.: US 11,090,485 B2
(45) Date of Patent: Aug. 17, 2021

(54) SYSTEMS AND METHODS FOR INTRA-SURGICAL MONITORING OF EVOKED RESPONSES THAT OCCUR DURING AN ELECTRODE LEAD INSERTION PROCEDURE

(71) Applicants: Kanthaiah Koka, Valencia, CA (US); Leonid M. Litvak, Los Angeles, CA (US); ADVANCED BIONICS AG, Staefa (CH)

(72) Inventors: Kanthaiah Koka, Valencia, CA (US); Leonid M. Litvak, Los Angeles, CA (US)

(73) Assignee: Advanced Bionics AG, Staefa (CH)

(\*) Notice: Subject to any disclaimer, the term of this patent is extended or adjusted under 35 U.S.C. 154(b) by 491 days.

(21) Appl. No.: 15/768,492

(22) PCT Filed: Nov. 3, 2015

(86) PCT No.: PCT/US2015/058879
§ 371 (c)(1),
(2) Date: Apr. 13, 2018

(87) PCT Pub. No.: WO2017/065809
PCT Pub. Date: Apr. 20, 2017

(65) Prior Publication Data
US 2018/0304069 A1 Oct. 25, 2018

Related U.S. Application Data

(60) Provisional application No. 62/241,054, filed on Oct. 13, 2015.

(51) Int. Cl.
*A61N 1/05* (2006.01)
*A61N 1/36* (2006.01)
*A61B 5/38* (2021.01)

(52) U.S. Cl.
CPC ....... *A61N 1/0541* (2013.01); *A61N 1/36039* (2017.08); *A61B 5/38* (2021.01)

(58) Field of Classification Search
CPC .............. A61N 1/0541; A61N 1/36036; A61N 1/36039; A61B 5/04845
See application file for complete search history.

(56) References Cited

U.S. PATENT DOCUMENTS 8,086,319 B2 12/2011 Van Dijk
9,072,468 B2 7/2015 Buchman et al.
(Continued)

FOREIGN PATENT DOCUMENTS

WO    02/32498      4/2002
WO    2015054149   4/2015
(Continued)

OTHER PUBLICATIONS

Davis, An Active Process in Cochlear Mechanics, (1983). An active process in cochlear mechanics. Hearing research, 9(1), 79-90.
(Continued)

*Primary Examiner* — Daniel L Cerioni
*Assistant Examiner* — Raymond P Dulman
(74) *Attorney, Agent, or Firm* — ALG Intellectual Property, LLC

(57) ABSTRACT

An exemplary monitoring system 1) receives a user input command to begin monitoring evoked responses that occur in response to acoustic stimulation during an insertion procedure in which a lead that is communicatively coupled to a cochlear implant is inserted into a cochlea of a patient, the lead having an array of intracochlear electrodes and an extracochlear electrode, the extracochlear electrode physically and communicatively coupled to a probe that is also communicatively coupled to the monitoring system, 2) directs, in response to the user input command, the cochlear (Continued)

implant to short an intracochlear electrode with the extracochlear electrode, 3) presents the acoustic stimulation to the patient, and 4) records the evoked responses that occur in response to the acoustic stimulation by using the intracochlear electrode to detect signals representative of the evoked responses and receiving the detected signals by way of the extracochlear electrode and the probe.

18 Claims, 14 Drawing Sheets

(56) References Cited

U.S. PATENT DOCUMENTS

| | | | |
|---|---|---|---|
| 2005/0137639 A1 | 6/2005 | Havel | |
| 2006/0235332 A1* | 10/2006 | Smoorenburg | A61N 1/37247 600/559 |
| 2006/0287690 A1 | 12/2006 | Bouchataoui et al. | |
| 2007/0167691 A1* | 7/2007 | Causevic | A61B 5/24 600/301 |
| 2009/0259140 A1 | 10/2009 | Buchman | |
| 2010/0030012 A1* | 2/2010 | Meskens | H04R 25/554 600/25 |
| 2010/0114288 A1 | 5/2010 | Haller et al. | |
| 2010/0198301 A1* | 8/2010 | Smith | A61N 1/36038 607/57 |
| 2010/0280307 A1* | 11/2010 | Lineaweaver | A61N 1/36038 600/25 |
| 2011/0087085 A1* | 4/2011 | Tsampazis | A61N 1/36039 600/379 |
| 2011/0288613 A1* | 11/2011 | Smith | A61N 1/37264 607/57 |
| 2012/0143284 A1* | 6/2012 | Capcelea | A61N 1/36038 607/57 |
| 2014/0107441 A1 | 4/2014 | Grasso et al. | |
| 2014/0276194 A1 | 9/2014 | Osorio | |
| 2015/0018699 A1* | 1/2015 | Zeng | A61B 5/0402 600/509 |
| 2015/0051654 A1* | 2/2015 | Litvak | A61B 5/121 607/3 |
| 2015/0224312 A1* | 8/2015 | Platz | H04R 25/554 607/57 |
| 2015/0258337 A1* | 9/2015 | Long | A61N 1/36038 607/57 |
| 2016/0199638 A1* | 7/2016 | Xu | A61N 1/36036 607/137 |

FOREIGN PATENT DOCUMENTS

| | | |
|---|---|---|
| WO | 2015/130318 | 9/2015 |
| WO | 2015/130319 | 9/2015 |
| WO | 2017/182931 | 10/2017 |

OTHER PUBLICATIONS

Chertoff et al, Analysis of the Cochlear Microphonic to a Low-Frequency Tone Embedded in Filtered Noise, The Journal of the Acoustical Society of America, 132(5), 3351-62.

International Search Report and Written Opinion received in International Application No. PCT/US15/058879, dated Jun. 9, 2016.

International Search Report and Written Opinion received in International Application No. PCT/US16/015203, dated Jun. 14, 2016.

Kohllbffel, Longitudinal Amplitude and Phase Distribution of the Cochlear Microphonic (Guinea Pig) and Spatial Filtering, Journal of Sound and Vibration, vol. 11, Issue 3, Mar. 1970, pp. 325-334.

Tasaki et al, The Space-Time Pattern of the Cochlear Microphonics (Guinea Pig), as Recorded by Differential Electrodes, J. Acoust. Soc. Am. vol. 24, Issue 5, pp. 502-519 (1952).

* cited by examiner

SYSTEMS AND METHODS FOR INTRA-SURGICAL MONITORING OF EVOKED RESPONSES THAT OCCUR DURING AN ELECTRODE LEAD INSERTION PROCEDURE

RELATED APPLICATIONS

The present application claims priority to U.S. Provisional Patent Application No. 62/241,054, filed Oct. 13, 2015, the contents of which are hereby incorporated by reference in their entirety.

BACKGROUND INFORMATION

Intra-operative evoked potential machines are sometimes used to monitor electrocochlear ("ECoG") potentials that occur before and during surgical insertion of an electrode lead into a cochlear implant patient. These ECoG potentials are used to monitor and ascertain trauma that may occur to the cochlea during the insertion procedure, as well as residual hearing of different areas of the cochlea as the electrode lead is inserted. Conventionally, ECoG potentials are measured by placing an electrode at the promontory of the tympanic cavity, at the round window within the ear, or at the oval window within the ear.

Unfortunately, the potentials measured at any of these placement sites are smaller than potentials that occur within the cochlea itself, thereby making it harder for the evoked potential machines to record them. Moreover, because the potentials are relatively small, they must be monitored for a relatively long period of time in order to provide enough averaging to achieve acceptable signal to noise ("SNR") ratios. This relatively long period of time may make the surgeon performing the insertion procedure wait an undesirable or unacceptable amount of time to receive the feedback that he or she needs to continue with the procedure. Finally, placement of an electrode at the promontory of the tympanic cavity, the round window, or the oval window may obstruct the surgeon's view of the electrode lead during the insertion procedure.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Figure 1:
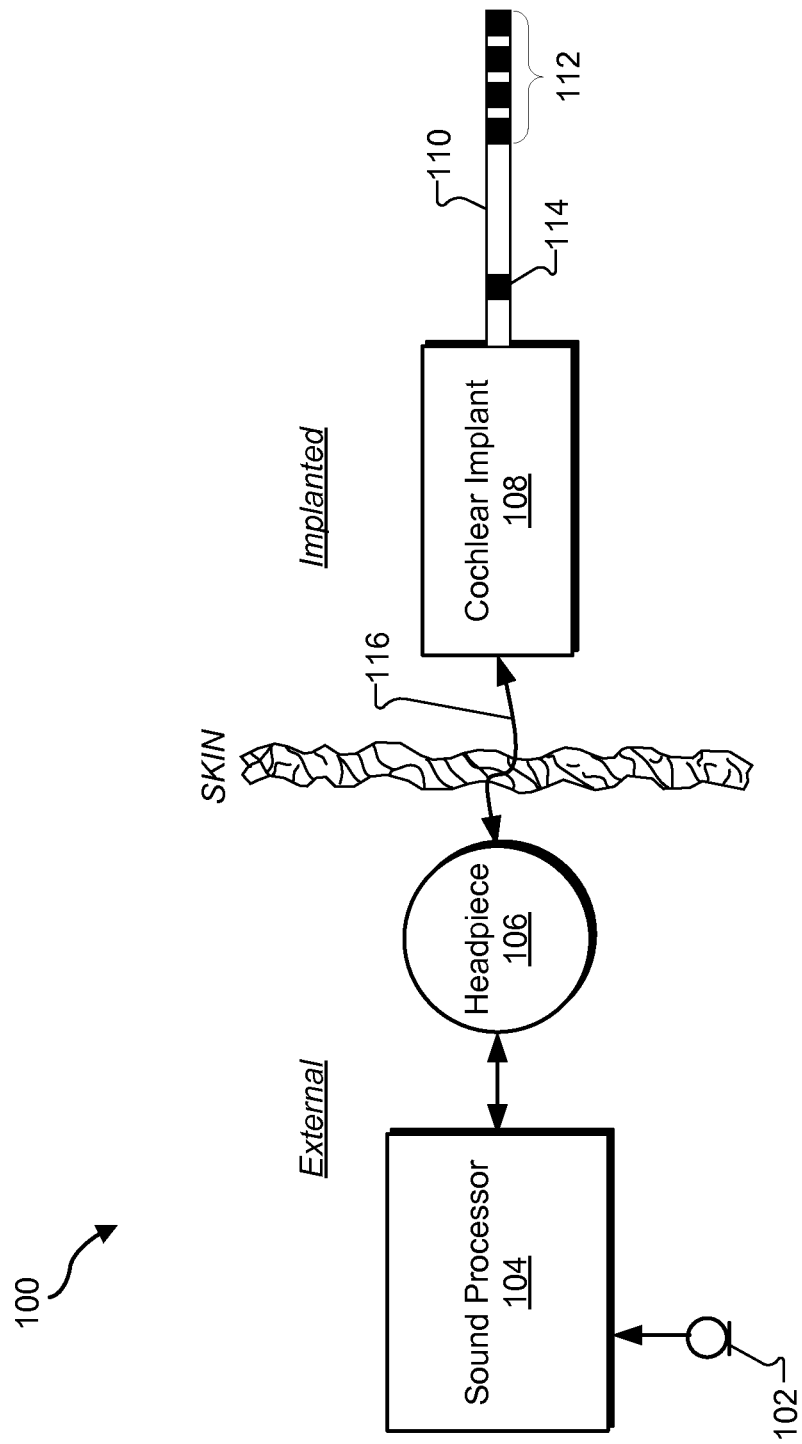
FIG. 1 illustrates an exemplary auditory prosthesis system according to principles described herein.

Systems and methods for intra-surgical monitoring of evoked responses that occur during an electrode lead insertion procedure are described herein. For example, an exemplary monitoring system implemented by at least one physical computing device may receive a user input command to begin monitoring evoked responses that occur in response to acoustic stimulation during an insertion procedure in which an electrode lead (or simply "lead") that is communicatively coupled to a cochlear implant is inserted into a cochlea of a patient. As will be described below, the lead may have an array of intracochlear electrodes disposed on a distal portion of the lead and that are configured to be located within the cochlea when the insertion procedure is completed. The lead may also include an extracochlear electrode (e.g., a ring electrode) configured to be located external to the cochlea when the insertion procedure is completed. In some examples, the extracochlear electrode may be physically and communicatively coupled to a probe (e.g., by way of a clip connection that may be temporarily connected to the extracochlear electrode).

In response to the user input command, the monitoring system may direct the cochlear implant to short an intracochlear electrode included in the array of intracochlear electrodes with the extracochlear electrode. For example, the monitoring system may transmit a command to the cochlear implant by way of a sound processor that is in wireless communication with the cochlear implant. The command may be configured to direct the cochlear implant to temporarily short the intracochlear electrode with the extracochlear electrode (e.g., by way of an electrode multiplexer included in the cochlear implant).

While the intracochlear electrode is shorted with the extracochlear electrode, the monitoring system may present the acoustic stimulation to the patient by way of a loudspeaker. The loudspeaker may be placed, for example, in or near an entrance of the ear. The monitoring system may then record the evoked responses that occur in response to the acoustic stimulation by using the intracochlear electrode to detect signals representative of the evoked responses and receiving the detected signals by way of the extracochlear electrode and the probe.

Because an intracochlear electrode is used in accordance with the systems and methods described herein to detect the signals representative of the evoked responses, the detected evoked responses may have much higher amplitudes than evoked responses detected at extracochlear locations (e.g., the promontory of the tympanic cavity, the round window, or the oval window). This may result in faster processing of the evoked responses, which, in turn, may be beneficial to a surgeon needing substantially real-time feedback as he or she inserts the electrode lead. Moreover, the systems and methods described herein do not require an additional recording electrode not disposed on the electrode lead and that might obstruct a surgeon's view of the electrode lead during the insertion procedure.

As used herein, an "evoked response" refers to an intracochlear hair-cell response (i.e., cochlear microphonics), a neural response (e.g., an auditory nerve response, a brainstem response, a compound action potential), an ECoG potential, and/or any other type of neural or physiological response that may occur within a patient in response to application of acoustic stimulation to the patient.

FIG. 1 illustrates an exemplary auditory prosthesis system 100. Auditory prosthesis system 100 may include a microphone 102, a sound processor 104, a headpiece 106 having a coil disposed therein, a cochlear implant 108, and an electrode lead 110 (also referred to as a "lead"). Lead 110 includes an array of intracochlear electrodes 112 disposed on a distal portion of lead 110 and that are configured to be located within the cochlea after the lead 110 is inserted into the cochlea. Lead 110 also includes an extracochlear electrode 114 configured to be located external to the cochlea after insertion of lead 110. Extracochlear electrode 114 may be used, in some examples, as a return electrode for electrical stimulation applied via one or more of intracochlear electrodes 112. While lead 110 is shown to be straight, it will be recognized that lead 110 may alternatively be pre-curved so as to fit within the cochlea. Additional or alternative components may be included within auditory prosthesis system 100 as may serve a particular implementation.

As shown, auditory prosthesis system 100 may include various components configured to be located external to a patient including, but not limited to, microphone 102, sound processor 104, and headpiece 106. Auditory prosthesis system 100 may further include various components configured to be implanted within the patient including, but not limited to, cochlear implant 108 and electrode lead 110.

Microphone 102 may be configured to detect audio signals presented to the user. Microphone 102 may be implemented in any suitable manner. For example, microphone 102 may include a microphone that is configured to be placed within the concha of the ear near the entrance to the ear canal, such as a T-MIC™ microphone from Advanced Bionics. Such a microphone may be held within the concha of the ear near the entrance of the ear canal by a boom or stalk that is attached to an ear hook configured to be selectively attached to sound processor 104. Additionally or alternatively, microphone 102 may be implemented by one or more microphones disposed within headpiece 106, one or more microphones disposed within sound processor 104, one or more beam-forming microphones, and/or any other suitable microphone as may serve a particular implementation.

Sound processor 104 (i.e., one or more components included within sound processor 104) may be configured to direct cochlear implant 108 to generate and apply electrical stimulation (also referred to herein as "stimulation current") representative of one or more audio signals (e.g., one or more audio signals detected by microphone 102, input by way of an auxiliary audio input port, input by way of a CPI, etc.) to one or more stimulation sites associated with an auditory pathway (e.g., the auditory nerve) of the patient. Exemplary stimulation sites include, but are not limited to, one or more locations within the cochlea, the cochlear nucleus, the inferior colliculus, and/or any other nuclei in the auditory pathway. To this end, sound processor 104 may process the one or more audio signals in accordance with a selected sound processing strategy or program to generate appropriate stimulation parameters for controlling cochlear implant 108. Sound processor 104 may be housed within any suitable housing (e.g., a behind-the-ear ("BTE") unit, a body worn device, and/or any other sound processing unit as may serve a particular implementation).

In some examples, sound processor 104 may wirelessly transmit stimulation parameters (e.g., in the form of data words included in a forward telemetry sequence) and/or power signals to cochlear implant 108 by way of a wireless communication link 116 between headpiece 106 and cochlear implant 108. It will be understood that communication link 116 may include a bi-directional communication link and/or one or more dedicated uni-directional communication links.

Headpiece 106 may be communicatively coupled to sound processor 104 and may include an external antenna (e.g., a coil and/or one or more wireless communication components) configured to facilitate selective wireless coupling of sound processor 104 to cochlear implant 108. Headpiece 106 may additionally or alternatively be used to selectively and wirelessly couple any other external device to cochlear implant 108. To this end, headpiece 106 may be configured to be affixed to the patient's head and positioned such that the external antenna housed within headpiece 106 is communicatively coupled to a corresponding implantable antenna (which may also be implemented by a coil and/or one or more wireless communication components) included within or otherwise associated with cochlear implant 108. In this manner, stimulation parameters and/or power signals may be wirelessly transmitted between sound processor 104 and cochlear implant 108 via a communication link 116 (which may include a bi-directional communication link and/or one or more dedicated uni-directional communication links as may serve a particular implementation).

Cochlear implant 108 may include any type of implantable stimulator that may be used in association with the systems and methods described herein. For example, cochlear implant 108 may be implemented by an implantable cochlear stimulator. In some alternative implementations, cochlear implant 108 may include a brainstem implant and/or any other type of cochlear implant that may be implanted within a patient and configured to apply stimulation to one or more stimulation sites located along an auditory pathway of a patient.

In some examples, cochlear implant 108 may be configured to generate electrical stimulation representative of an audio signal processed by sound processor 104 (e.g., an audio signal detected by microphone 102) in accordance with one or more stimulation parameters transmitted thereto by sound processor 104. Cochlear implant 108 may be further configured to apply the electrical stimulation to one or more stimulation sites (e.g., one or more intracochlear regions) within the patient via one or more intracochlear electrodes 112 disposed along electrode lead 110. In some examples, cochlear implant 108 may include a plurality of independent current sources each associated with a channel defined by one or more of intracochlear electrodes 112. In this manner, different stimulation current levels may be applied to multiple stimulation sites simultaneously by way of multiple intracochlear electrodes 112.

Figure 2:
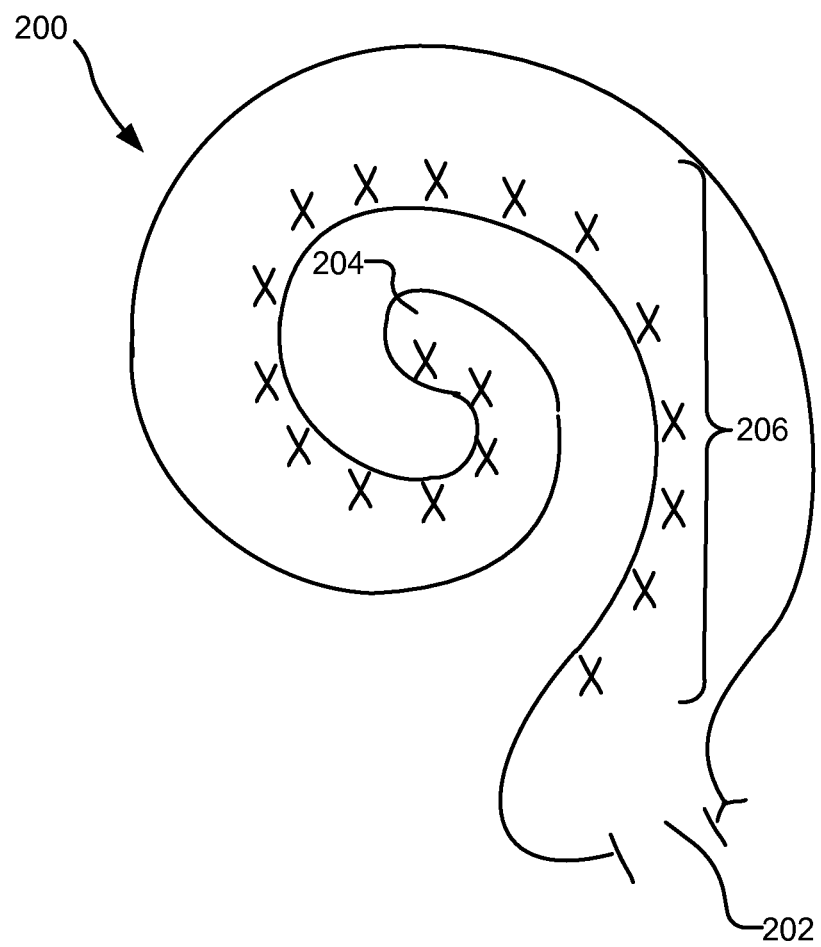
FIG. 2 illustrates a schematic structure of the human cochlea according to principles described herein.

FIG. 2 illustrates a schematic structure of the human cochlea 200 into which electrode lead 110 may be inserted. As shown in FIG. 2, the cochlea 200 is in the shape of a spiral beginning at a base 202 and ending at an apex 204. Within the cochlea 200 resides auditory nerve tissue 206, which is denoted by Xs in FIG. 2. The auditory nerve tissue 206 is organized within the cochlea 200 in a tonotopic manner. Relatively low frequencies are encoded at or near the apex 204 of the cochlea 200 (referred to as an "apical region") while relatively high frequencies are encoded at or near the base 202 (referred to as a "basal region"). Hence, electrical stimulation applied by way of electrodes disposed within the apical region (i.e., "apical electrodes") may result in the patient perceiving relatively low frequencies and electrical stimulation applied by way of electrodes disposed within the basal region (i.e., "basal electrodes") may result in the patient perceiving relatively high frequencies. The delineation between the apical and basal electrodes on a particular electrode lead may vary depending on the insertion depth of the electrode lead, the anatomy of the patient's cochlea, and/or any other factor as may serve a particular implementation.

The auditory prosthesis system 100 illustrated in FIG. 1 may be referred to as a cochlear implant system because sound processor 104 is configured to direct cochlear implant 108 to generate and apply electrical stimulation representative of audio content (e.g., one or more audio signals) to one or more stimulation sites within the patient by way of one or more of electrodes 112.

Figure 3:
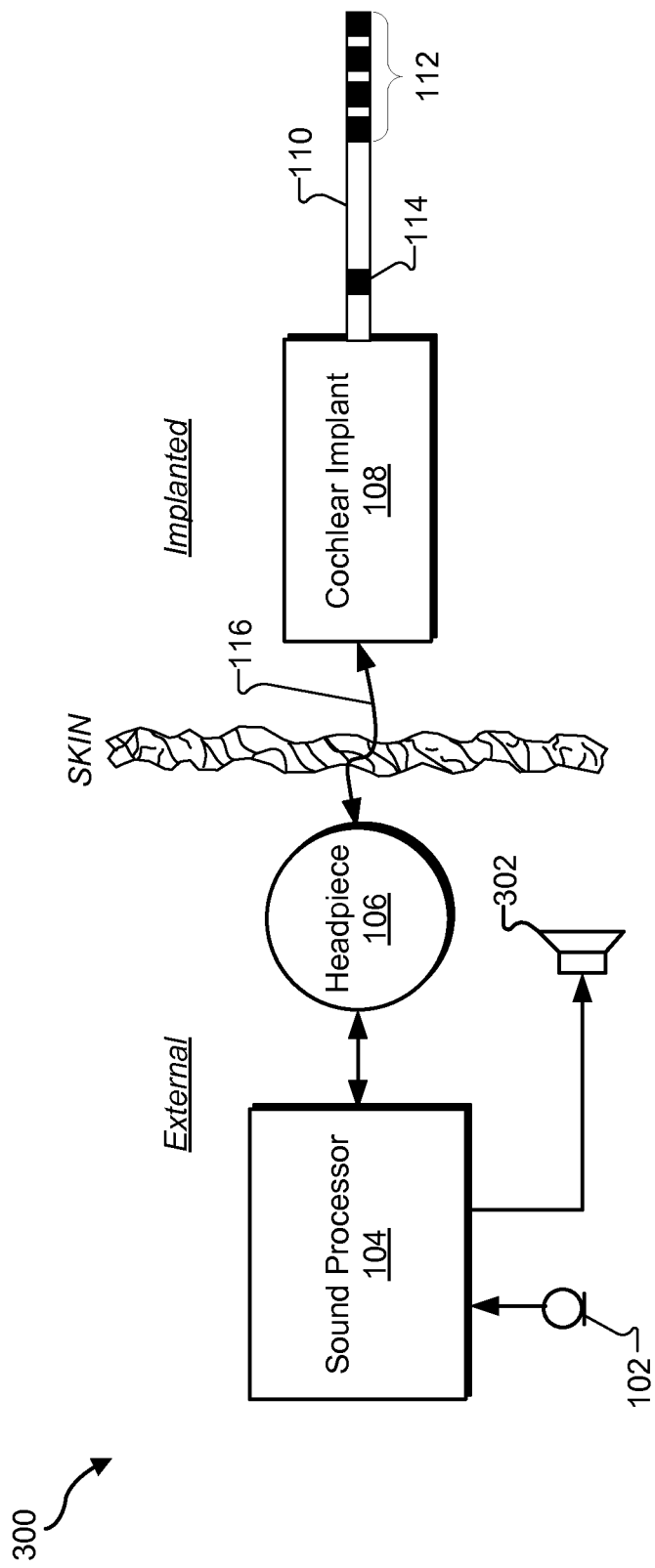
FIG. 3 illustrates an exemplary implementation of the auditory prosthesis system of FIG. 1 according to principles described herein.

FIG. 3 illustrates an exemplary implementation 300 of auditory prosthesis system 100 in which auditory prosthesis system 100 is further configured to provide acoustic stimulation to the patient. Hence, implementation 300 shown in FIG. 3 may be referred to as an electro-acoustic stimulation ("EAS") system.

As shown, implementation 300 may further include a loudspeaker 302 (also referred to as a "receiver"). Loudspeaker 302 may be in communication with an ear of the patient (e.g., located at an entrance or within the ear canal of the patient). In this configuration, sound processor 104 (which, in implementation 300, may be referred to as an "EAS sound processor") may be configured to direct loudspeaker 302 to apply acoustic stimulation representative of audio content included in relatively low frequency bands (e.g., below 1000 Hz) to the patient and cochlear implant 108 to apply electrical stimulation representative of audio content included in relatively high frequency bands (e.g., above 1000 Hz) to one or more stimulation sites within the patient by way of one or more of intracochlear electrodes 112.

In some examples, a programming system separate from (i.e., not included within) auditory prosthesis system 100 may be selectively and communicatively coupled to sound processor 104 in order to perform one or more programming or fitting operations with respect to auditory prosthesis system 100. For example, the programming system may present audio clips to the patient by way of the auditory prosthesis system in order to facilitate evaluation of how well the auditory prosthesis system is performing for the patient.

Figure 4:
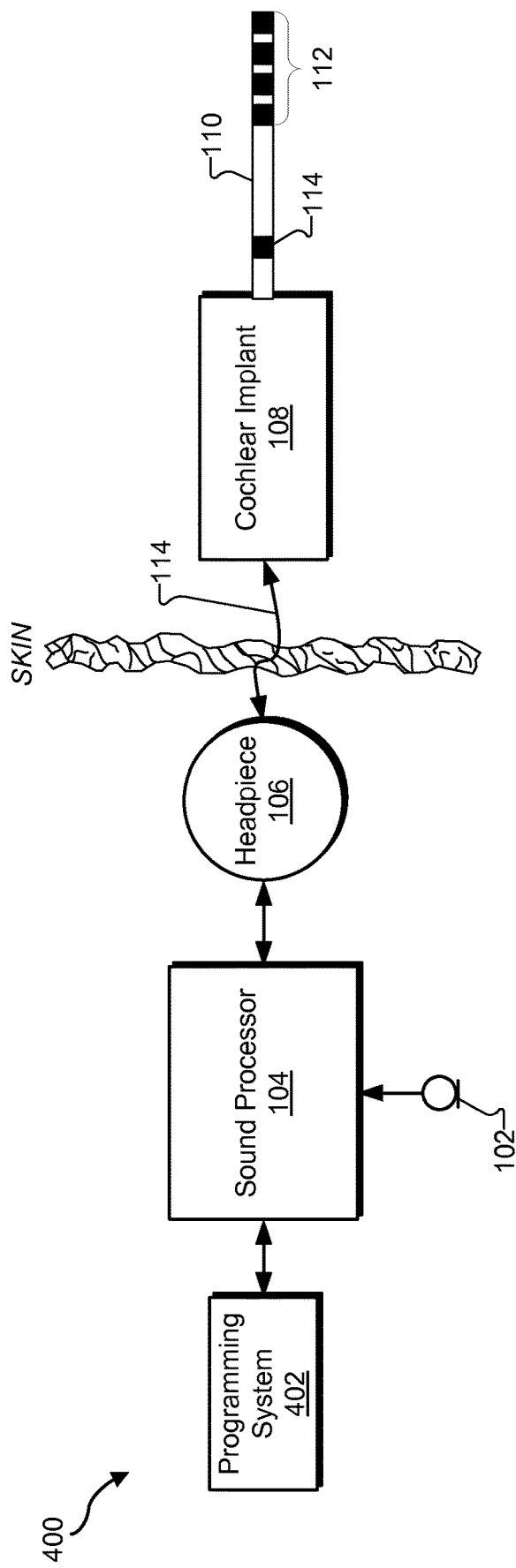
FIG. 4 shows an exemplary configuration in which a programming system is communicatively coupled to a sound processor according to principles described herein.

To illustrate, FIG. 4 shows an exemplary configuration 400 in which a programming system 402 is communicatively coupled (e.g., by way of a wired or wireless communication channel) to sound processor 104. Programming system 402 may be implemented by any suitable combination of physical computing and communication devices including, but not limited to, a fitting station or device, a programming device, a personal computer, a laptop computer, a handheld device, a mobile device (e.g., a mobile phone), a clinician's programming interface ("CPI") device, and/or any other suitable component as may serve a particular implementation. In some examples, programming system 402 may provide one or more graphical user interfaces ("GUIs") (e.g., by presenting the one or more GUIs by way of a display screen) with which a clinician or other user may interact.

Figure 5:
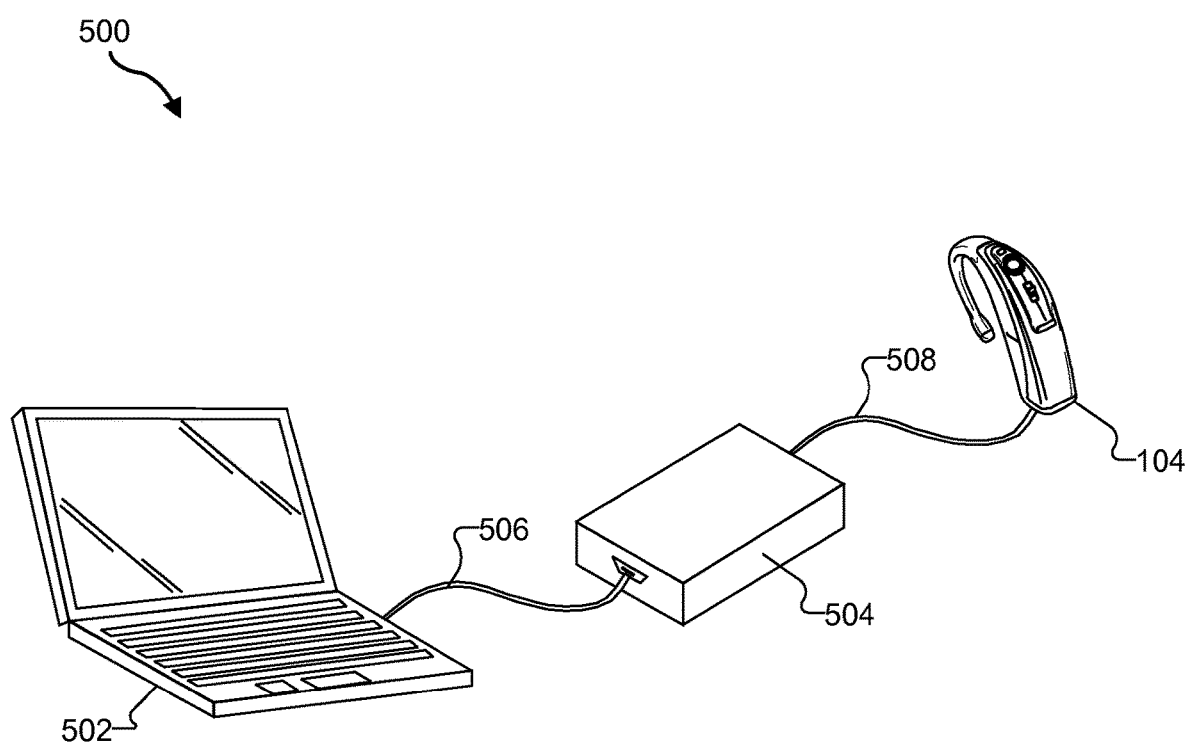
FIG. 5 illustrates an exemplary implementation of a programming system according to principles described herein.

FIG. 5 illustrates an exemplary configuration 500 in which programming system 402 is implemented by a computing device 502 and a CPI device 504. As shown, computing device 502 may be selectively and communicatively coupled to CPI device 504 by way of a cable 506. Likewise, CPI device 504 may be selectively and communicatively coupled to sound processor 104 by way of a cable 508. Cables 506 and 508 may each include any suitable type of cable that facilitates transmission of digital data between computing device 502 and sound processor 104. For example, cable 506 may include a universal serial bus ("USB") cable and cable 508 may include any type of cable configured to connect to a programming port included in sound processor 104.

Figure 6:
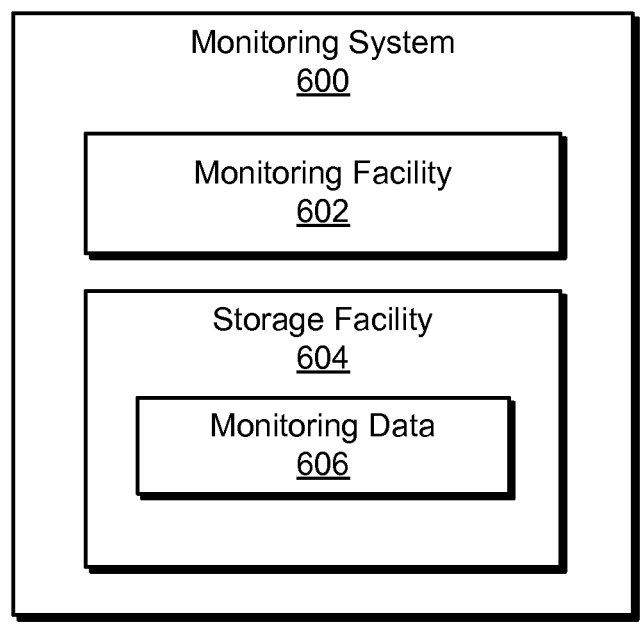
FIG. 6 illustrates exemplary components of a monitoring system according to principles described herein.

FIG. 6 illustrates exemplary components of a monitoring system 600. Monitoring system 600 may be configured to perform any of the operations described herein. As shown, monitoring system 600 may include a monitoring facility 602 and a storage facility 604, which may be in communication with one another using any suitable communication technologies. Storage facility 604 may maintain monitoring data 606 generated and/or used by monitoring facility 602. Storage facility 604 may maintain additional or alternative data as may serve a particular implementation.

Monitoring facility 602 may perform various operation associated with intra-surgical monitoring of evoked responses that occur during an electrode lead insertion procedure.

For example, monitoring facility 602 may receive a user input command to begin monitoring evoked responses that occur in response to acoustic stimulation during an insertion procedure in which a lead that is communicatively and physically coupled to a cochlear implant is inserted into a cochlea of a patient. As described above, the lead may have array of intracochlear electrodes (e.g., intracochlear electrodes 112) disposed on a distal portion of the lead that are configured to be located within the cochlea when the insertion procedure is completed. The lead may also have an extracochlear electrode (e.g., extracochlear electrode 114) configured to be located external to the cochlea when the insertion procedure is completed. As will be described below, the extracochlear electrode may be physically and communicatively coupled to a probe that is also communicatively coupled to monitoring system 600. Exemplary manners in which the user input command may be received by monitoring facility 602 will be described in more detail below.

In response to the user input command, monitoring facility 602 may direct the cochlear implant to short an intracochlear electrode included in the array of intracochlear electrodes with the extracochlear electrode. For example, monitoring facility 602 may transmit a command by way of a sound processor to the cochlear implant for the cochlear implant to short the intracochlear electrode with the extracochlear electrode. The cochlear implant may short the intracochlear electrode with the extracochlear electrode in any suitable manner. For example, the cochlear implant may utilize a multiplexer included in the cochlear implant to short the intracochlear electrode with the extracochlear electrode.

While the intracochlear electrode is shorted with the extracochlear electrode, monitoring facility 602 may present acoustic stimulation to the patient by way of a loudspeaker. Exemplary manners in which monitoring facility 602 may present acoustic stimulation to the patient by way of a loudspeaker will be described in more detail below.

Monitoring facility 602 may record the evoked responses that occur in response to the acoustic stimulation. For example, because the intracochlear electrode and the extracochlear electrode are shorted, monitoring facility 602 may use the intracochlear electrode to detect signals representative of the evoked responses from within the cochlea and receive the detected signals by way of the extracochlear electrode and the probe. This will be described in more detail below.

FIGS. 7-10 illustrate various implementations of monitoring system 600. Each implementation will now be described.

Figure 7:
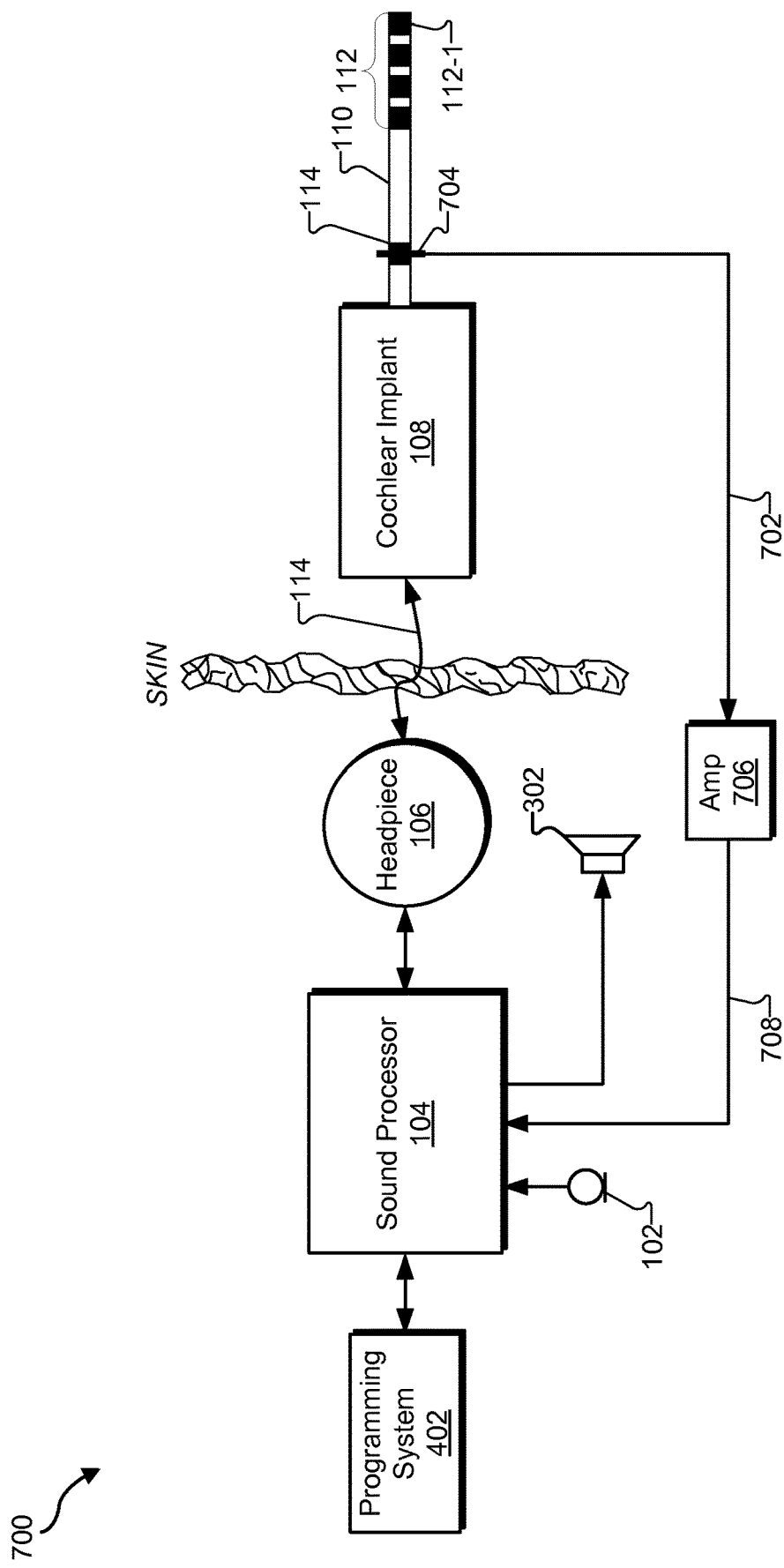
FIGS. 7-11 illustrate an exemplary implementations of the monitoring system of FIG. 6 according to principles described herein.

FIG. 7 illustrates an exemplary implementation 700 of monitoring system 600 in which monitoring system 600 is at least partially implemented by programming system 402 and sound processor 104 included in an EAS system. As will be described below, in implementation 700, sound processor 104 may both present the acoustic stimulation and record the evoked responses that occur in response to the acoustic stimulation.

As shown in FIG. 7, sound processor 104 is physically and communicatively coupled to loudspeaker 302. As also shown in FIG. 7, extracochlear electrode 114 is physically and communicatively coupled to a probe 702 by way of a clip connection 704 that may be removably (i.e., temporarily) connected to extracochlear electrode 114. Probe 702 may be communicatively coupled to sound processor 104 in any suitable manner. For example, as shown in FIG. 7, a distal end of probe 702 may be physically and communicatively coupled to an amplifier 706. Amplifier 706, in turn, may be communicatively coupled to sound processor 104 by way of a communication channel 708, which may be wired or wireless. It will be recognized that amplifier 706 may, in some embodiments, be omitted from implementation 700. In these cases, probe 702 may be physically coupled directly to sound processor 104.

In some examples, a user may provide a user input command for monitoring system 600 to begin monitoring evoked responses that occur in response to acoustic stimulation during an insertion procedure in which lead 110 is inserted into a cochlea of a patient. As mentioned above, lead 110 may be physically and communicatively coupled to cochlear implant 108 during the insertion procedure.

Programming system 402 may receive the user input command in any suitable manner. For example, programming system 402 may present a graphical user interface (e.g., by displaying the graphical user interface on a display screen) during the insertion procedure. The graphical user interface may include a selectable option to begin monitoring for the evoked responses. A user may select the option to provide the user input command. This will be described in more detail below.

Programming system 402 may transmit the user input command to sound processor 104. In response to receiving the user input command, sound processor 104 may direct cochlear implant 108 to short an intracochlear electrode included in the array of intracochlear electrodes 112 with extracochlear electrode 114. The directing may be performed, for example, by transmitting a command to cochlear implant 108 by way of a wireless link that communicatively couples sound processor 104 and cochlear implant 108 (e.g., by way of a wireless link between a coil disposed within headpiece 106 and a coil physically coupled to cochlear implant 108). For purposes of this example, sound processor 104 may direct cochlear implant 108 to short intracochlear electrode 112-1 with extracochlear electrode 114. However, it will be recognized that sound processor 104 may direct cochlear implant 108 to short any one of the intracochlear electrodes 112 with extracochlear electrode 114 as may serve a particular implementation.

In response to receiving the command from sound processor 104, cochlear implant 108 may short intracochlear electrode 112-1 with extracochlear electrode 114. While these electrodes are shorted together, sound processor 104 may present acoustic stimulation by way of loudspeaker 302. The acoustic stimulation may include any suitable acoustic stimulation (e.g., one or more tones).

Sound processor 104 may record evoked responses that occur in response to the acoustic stimulation. For example, sound processor 104 may receive, by way of extracochlear electrode 114 and probe 702, signals representative of the evoked responses as detected by intracochlear electrode 112-1. The signals detected by intracochlear electrode 112-1 may be analog signals. Hence, in some examples, sound processor 104 may convert the detected analog signals to digital signals by using an analog-to-digital converter included in sound processor 104 and that is also used by sound processor 104 to convert analog audio signals detected by microphone 102 into digital audio signals.

In some examples, sound processor 104 may transmit the digital signals representative of the evoked responses to programming system 402. Programming system 402 may use the digital signals to generate and present, within a graphical user interface, graphical information associated with the evoked responses. For example, as will be described in more detail below, the graphical information may include a graph that represents amplitudes of the evoked responses, a graph that represents a current time domain waveform of the evoked responses, and/or a graph that represents a current frequency domain waveform of the evoked responses.

In some examples, the signals detected by intracochlear electrode 112-1 may be amplified by amplifier 706 prior to sound processor 104 receiving the detected signals. For example, amplifier 706 may receive the detected signals by way of extracochlear electrode 114 and probe 702. Amplifier 706 may amplify the detected signals, which may result in a plurality of amplified signals. Amplifier 706 may transmit the amplified signals to sound processor 104 by way of communication channel 708. By amplifying the signals detected by intracochlear electrode 112-1, amplifier 706 may enable sound processor 104 to more effectively and efficiently process the signals. For example, amplification by amplifier 706 may make the signals large enough to be accurately converted from the analog domain to the digital domain. It will be recognized that although amplifier 706 is shown to be a stand-alone unit located outside sound processor 104, amplifier 706 may alternatively be located within sound processor 104.

Figure 8:
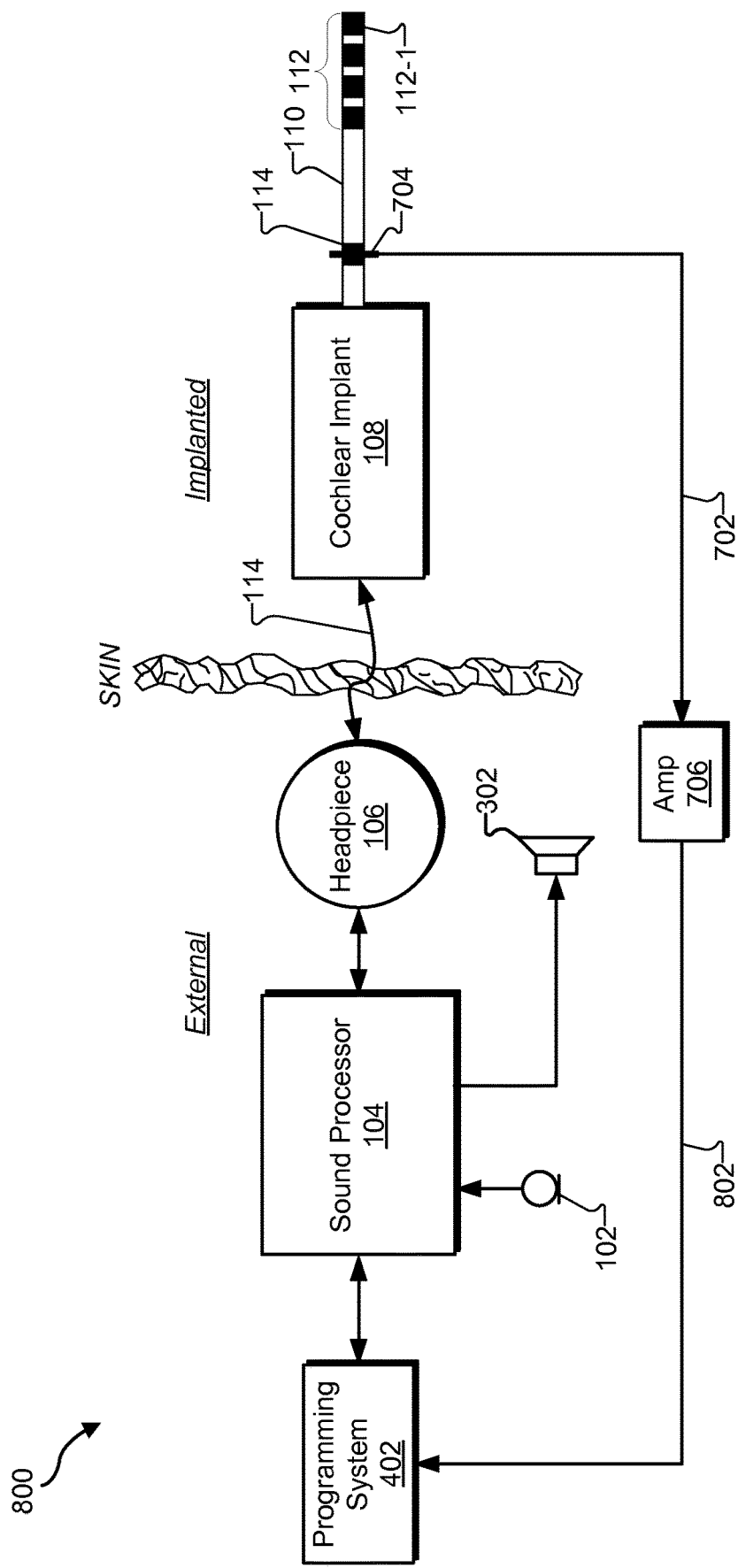

FIG. 8 illustrates another exemplary implementation 800 of monitoring system 600. Implementation 800 is similar to implementation 700, except that in implementation 800, sound processor 104 presents the acoustic stimulation and programming system 402 records the evoked responses that occur in response to the acoustic stimulation. To facilitate recording of the evoked responses by programming system 402, probe 702 may be communicatively coupled to programing system 402. For example, as shown in FIG. 8, a distal end of probe 702 may be physically and communicatively coupled to amplifier 706. Amplifier 706, in turn, may be communicatively coupled to programming system 402 by way of a communication channel 802 that is directly connected (e.g., physically or by way of a wireless connection) to programming system 402. It will be recognized that amplifier 706 may, in some embodiments, be omitted from implementation 800. In these cases, probe 702 may be physically coupled directly to programming system 402.

In this configuration, programming system 402 may receive and transmit to sound processor 104 a user input command to begin monitoring evoked responses in any of the ways described herein. In response to receiving the user input command, sound processor 104 may direct cochlear implant 108 to short intracochlear electrode 112-1 with extracochlear electrode 114, as described above.

In response to receiving the command from sound processor 104, cochlear implant 108 may short intracochlear electrode 112-1 with extracochlear electrode 114 as described above. While these electrodes are shorted together, sound processor 104 may present acoustic stimulation by way of loudspeaker 302. The acoustic stimulation may include any suitable acoustic stimulation (e.g., one or more tones).

Programming system 402 may record evoked responses that occur in response to the acoustic stimulation. For example, programming system 402 may receive, by way of extracochlear electrode 114 and probe 702, signals representative of the evoked responses as detected by intracochlear electrode 112-1. The signals detected by intracochlear electrode 112-1 may be analog signals. Hence, in some examples, programming system 402 may convert the detected analog signals to digital signals by using an analog-to-digital converter included in programming system 402.

As described above, the signals detected by intracochlear electrode 112-1 may be amplified by amplifier 706 prior to programming system 402 receiving the detected signals. For example, amplifier 706 may receive the detected signals by way of extracochlear electrode 114 and probe 702. Amplifier 706 may amplify the detected signals, which may result in a plurality of amplified signals. Amplifier 706 may transmit the amplified signals to programming system 402 by way of communication channel 802. By amplifying the signals detected by intracochlear electrode 112-1, amplifier 706 may enable programming system 402 to more effectively and efficiently process the signals. For example, amplification by amplifier 706 may make the signals large enough to be accurately converted from the analog domain to the digital domain. It will be recognized that although amplifier 706 is shown to be a stand-alone unit located outside programming system 402, amplifier 706 may alternatively be located within programming system 402.

Figure 9:
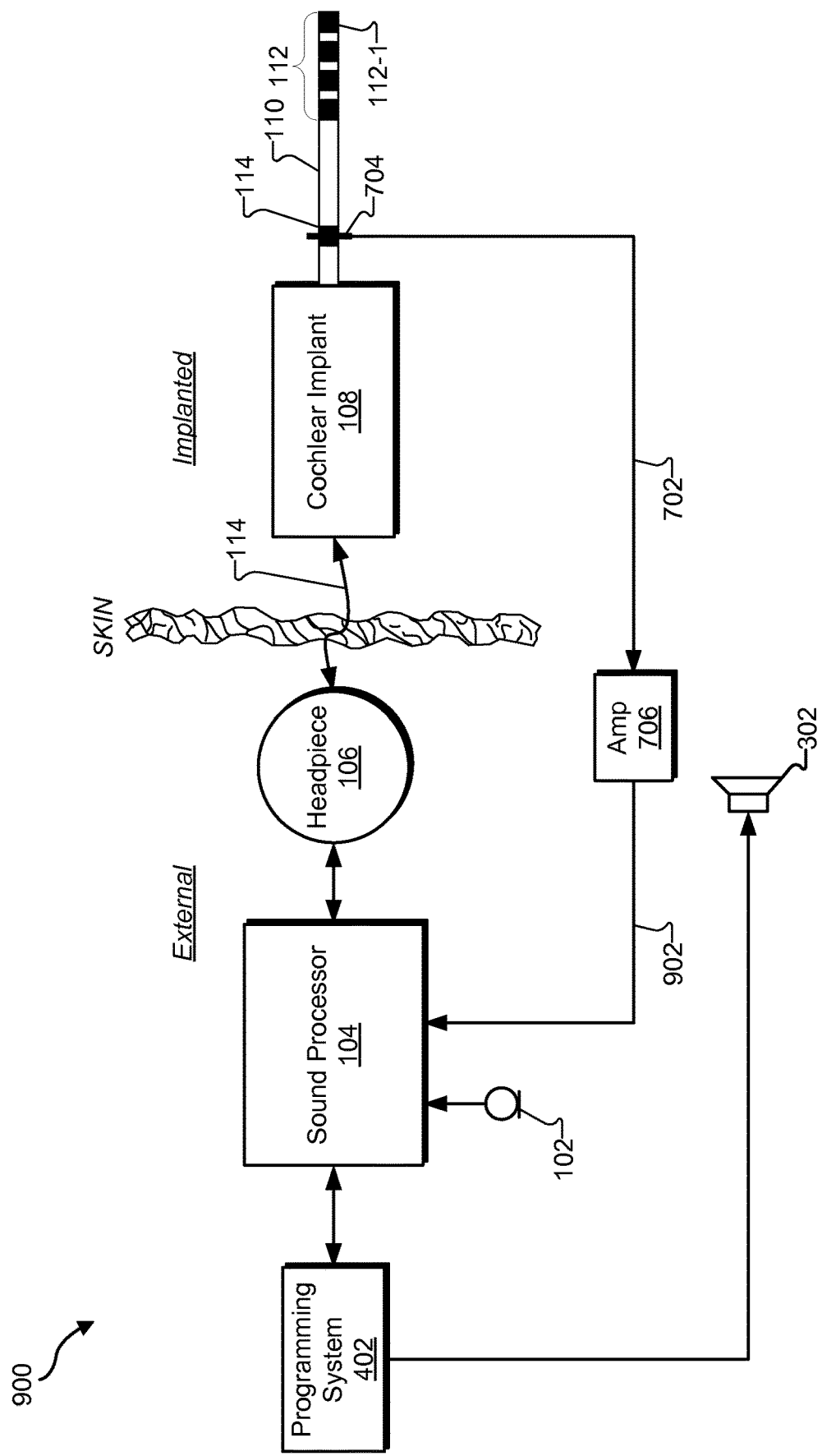

FIG. 9 illustrates another exemplary implementation 900 of monitoring system 600. Implementation 900 is similar to implementation 800, except that in implementation 900, programming system 402 presents the acoustic stimulation and sound processor 104 records the evoked responses that occur in response to the acoustic stimulation. To facilitate recording of the evoked responses by programming system 402, probe 702 may be communicatively coupled to sound processor 104. For example, as shown in FIG. 9, a distal end of probe 702 may be physically and communicatively coupled to amplifier 706. Amplifier 706, in turn, may be communicatively coupled to sound processor 104 by way of a communication channel 902 that is directly connected (e.g., physically or by way of a wireless connection) to sound processor 104. It will be recognized that amplifier 706 may, in some embodiments, be omitted from implementation 900. In these cases, probe 702 may be physically coupled directly to programming system 402.

In this configuration, programming system 402 may receive and transmit to sound processor 104 a user input command to begin monitoring evoked responses in any of the ways described herein. In response to receiving the user input command, sound processor 104 may direct cochlear implant 108 to short intracochlear electrode 112-1 with extracochlear electrode 114, as described above.

In response to receiving the command from sound processor 104, cochlear implant 108 may short intracochlear electrode 112-1 with extracochlear electrode 114 as described above. While these electrodes are shorted together, programming system 402 may present acoustic stimulation by way of loudspeaker 302. The acoustic stimulation may include any suitable acoustic stimulation (e.g., one or more tones).

Sound processor 104 may record evoked responses that occur in response to the acoustic stimulation. For example, sound processor 104 may receive, by way of extracochlear electrode 114 and probe 702, signals representative of the evoked responses as detected by intracochlear electrode 112-1. The signals detected by intracochlear electrode 112-1 may be analog signals. Hence, as described above, sound processor 104 may convert the detected analog signals to digital signals by using an analog-to-digital converter included in sound processor 104.

In some examples, sound processor 104 may transmit the digital signals representative of the evoked responses to programming system 402. Programming system 402 may use the digital signals to generate and present, within a graphical user interface, graphical information associated with the evoked responses.

As described above, the signals detected by intracochlear electrode 112-1 may be amplified by amplifier 706 prior to sound processor 104 receiving the detected signals. For example, amplifier 706 may receive the detected signals by way of extracochlear electrode 114 and probe 702. Amplifier 706 may amplify the detected signals, which may result in a plurality of amplified signals. Amplifier 706 may transmit the amplified signals to sound processor 104 by way of communication channel 902. By amplifying the signals detected by intracochlear electrode 112-1, amplifier 706 may enable sound processor 104 to more effectively and efficiently process the signals. For example, amplification by amplifier 706 may make the signals large enough to be accurately converted from the analog domain to the digital domain.

Figure 10:
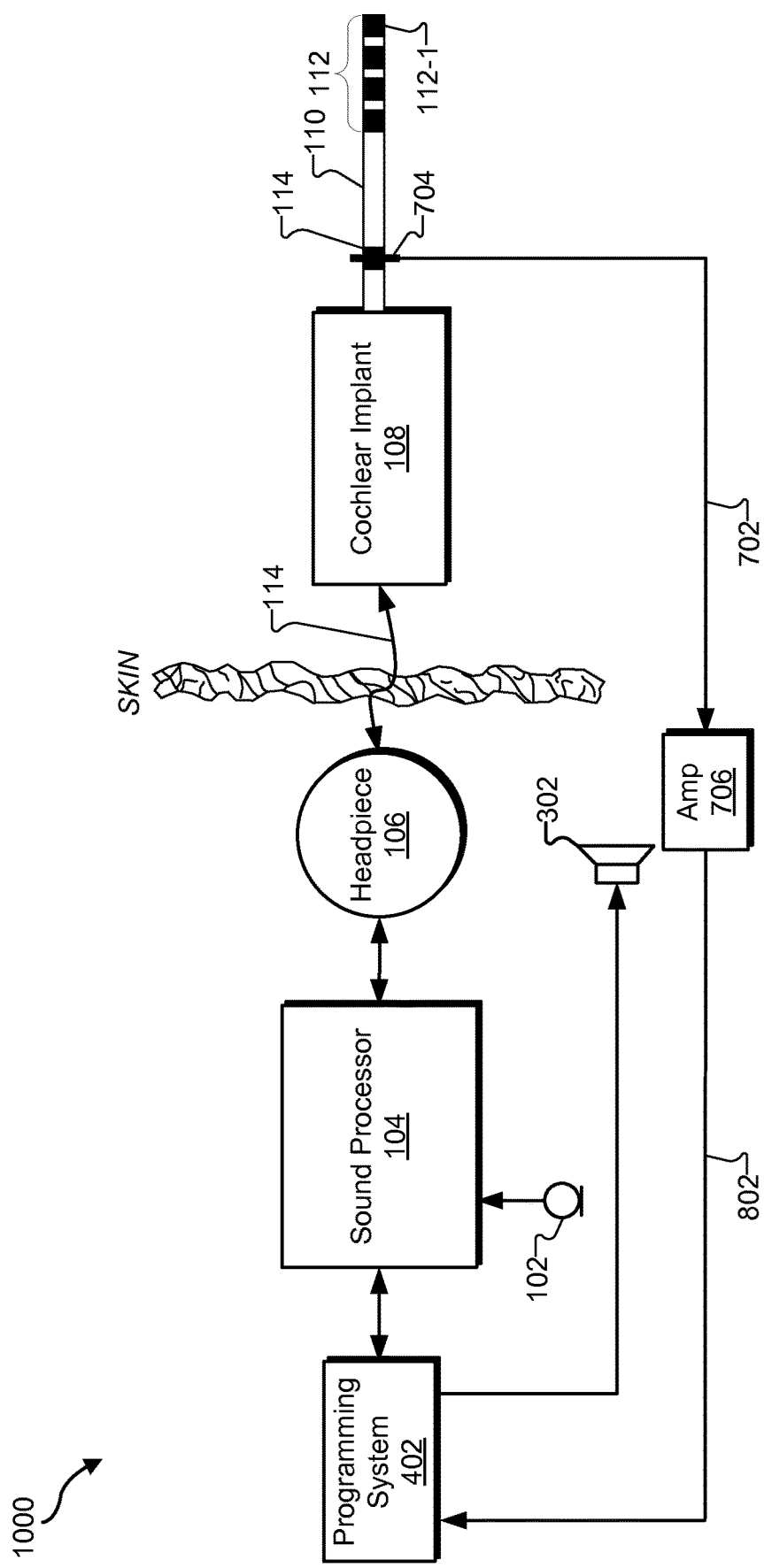

FIG. 10 illustrates another exemplary implementation 1000 of monitoring system 600. Implementation 1000 is similar to implementations 700, 800, and 900, except that in implementation 1000, programming system 402 both presents the acoustic stimulation and records the evoked responses that occur in response to the acoustic stimulation. Implementation 1000 may be useful, for example, when sound processor 104 is not an EAS sound processor (i.e., when sound processor 104 is not capable of providing acoustic stimulation).

In implementation 1000, loudspeaker 302 is physically and communicatively coupled to programming system 402 (and not to sound processor 104). Probe 702 is also communicatively coupled to programing system 402, as described above in connection with implementation 800. For example, as shown in FIG. 10, a distal end of probe 702 may be physically and communicatively coupled to amplifier 706. Amplifier 706, in turn, may be communicatively coupled to programming system 402 by way of communication channel 802 that is directly connected (e.g., physically or by way of a wireless connection) to programming system 402. It will be recognized that amplifier 706 may, in some embodiments, be omitted from implementation 1000. In these cases, probe 702 may be physically coupled directly to programming system 402.

In this configuration, programming system 402 may receive and transmit to sound processor 104 a user input command to begin monitoring evoked responses in any of the ways described herein. In response to receiving the user input command, sound processor 104 may direct cochlear implant 108 to short intracochlear electrode 112-1 with extracochlear electrode 114, as described above.

In response to receiving the command from sound processor 104, cochlear implant 108 may short intracochlear electrode 112-1 with extracochlear electrode 114 as described above. While these electrodes are shorted together, programming system 402 may present acoustic stimulation by way of loudspeaker 302. The acoustic stimulation may include any suitable acoustic stimulation (e.g., one or more tones).

Programming system 402 may record evoked responses that occur in response to the acoustic stimulation. For example, programming system 402 may receive, by way of extracochlear electrode 114 and probe 702, signals representative of the evoked responses as detected by intracochlear electrode 112-1. The signals detected by intracochlear electrode 112-1 may be analog signals. Hence, in some examples, programming system 402 may convert the detected analog signals to digital signals by using an analog-to-digital converter included in programming system 402.

As described above, the signals detected by intracochlear electrode 112-1 may be amplified by amplifier 706 prior to programming system 402 receiving the detected signals. For example, amplifier 706 may receive the detected signals by way of extracochlear electrode 114 and probe 702. Amplifier 706 may amplify the detected signals, which may result in a plurality of amplified signals. Amplifier 706 may transmit the amplified signals to programming system 402 by way of communication channel 802. By amplifying the signals detected by intracochlear electrode 112-1, amplifier 706 may enable programming system 402 to more effectively and efficiently process the signals. For example, amplification by amplifier 706 may make the signals large enough to be accurately converted from the analog domain to the digital domain.

Figure 11:
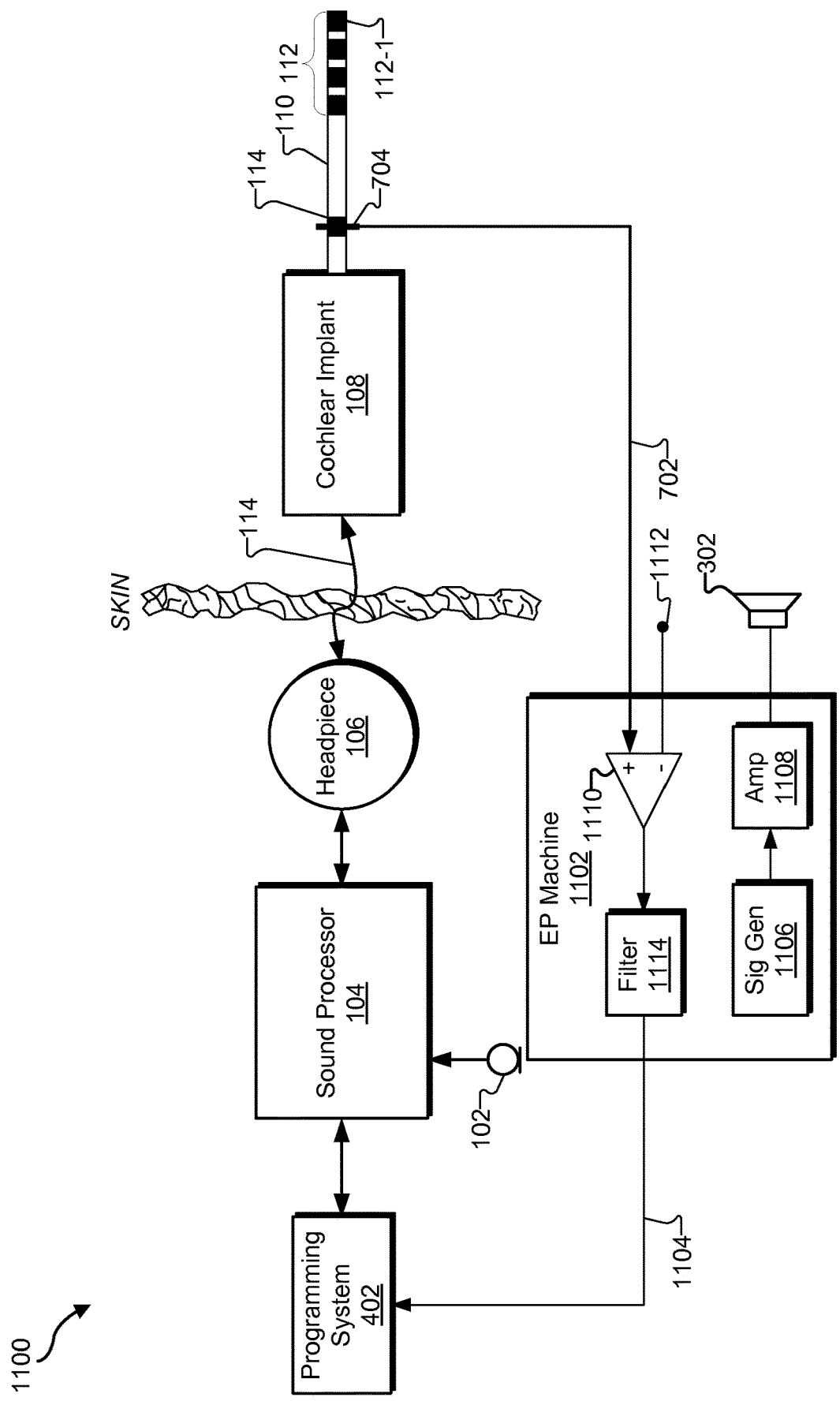

FIG. 11 illustrates another exemplary implementation 1100 of monitoring system 600. In implementation 1100, system 600 is at least partially implemented by an evoked potential ("EP") machine 1102, which may be physically separate from programing system 402 and sound processor 104. EP machine 1102 may be communicatively coupled to programming system 402 by way of a communication channel 1104 (which may be wired or wireless). In implementation 1100, EP machine 1102 may be configured to both present the acoustic stimulation and record the evoked responses that occur in response to the acoustic stimulation.

In implementation 1100, programming system 402 may receive and transmit to sound processor 104 a user input command to begin monitoring evoked responses in any of the ways described herein. In response to receiving the user input command, sound processor 104 may direct cochlear implant 108 to short intracochlear electrode 112-1 with extracochlear electrode 114, as described above.

In response to receiving the command from sound processor 104, cochlear implant 108 may short intracochlear electrode 112-1 with extracochlear electrode 114 as described above. While these electrodes are shorted together, EP machine 1102 may present acoustic stimulation by way of loudspeaker 302. The acoustic stimulation may include any suitable acoustic stimulation (e.g., one or more tones). As shown, the acoustic stimulation may be generated by a signal generator 1106 and amplified by an amplifier 1108, both of which may be included in EP machine.

EP machine 1102 may record evoked responses that occur in response to the acoustic stimulation. For example, EP machine 1102 may receive, by way of extracochlear electrode 114 and probe 702, signals representative of the evoked responses as detected by intracochlear electrode 112-1. The signals may be input into a first input of a differential amplifier 1110. As shown, the second input of the differential amplifier 1110 may be coupled to a ground electrode 1112. After the signals are amplified, the signals may be filtered by a filter 1114, which, in some examples, may also convert the detected signals into digital signals.

In some examples, EP machine 1102 may transmit digital signals representative of the evoked responses to programming system 402 by way of communication channel 1104. Programming system 402 may use the digital signals to generate and present, within a graphical user interface, graphical information associated with the evoked responses.

Figure 12:
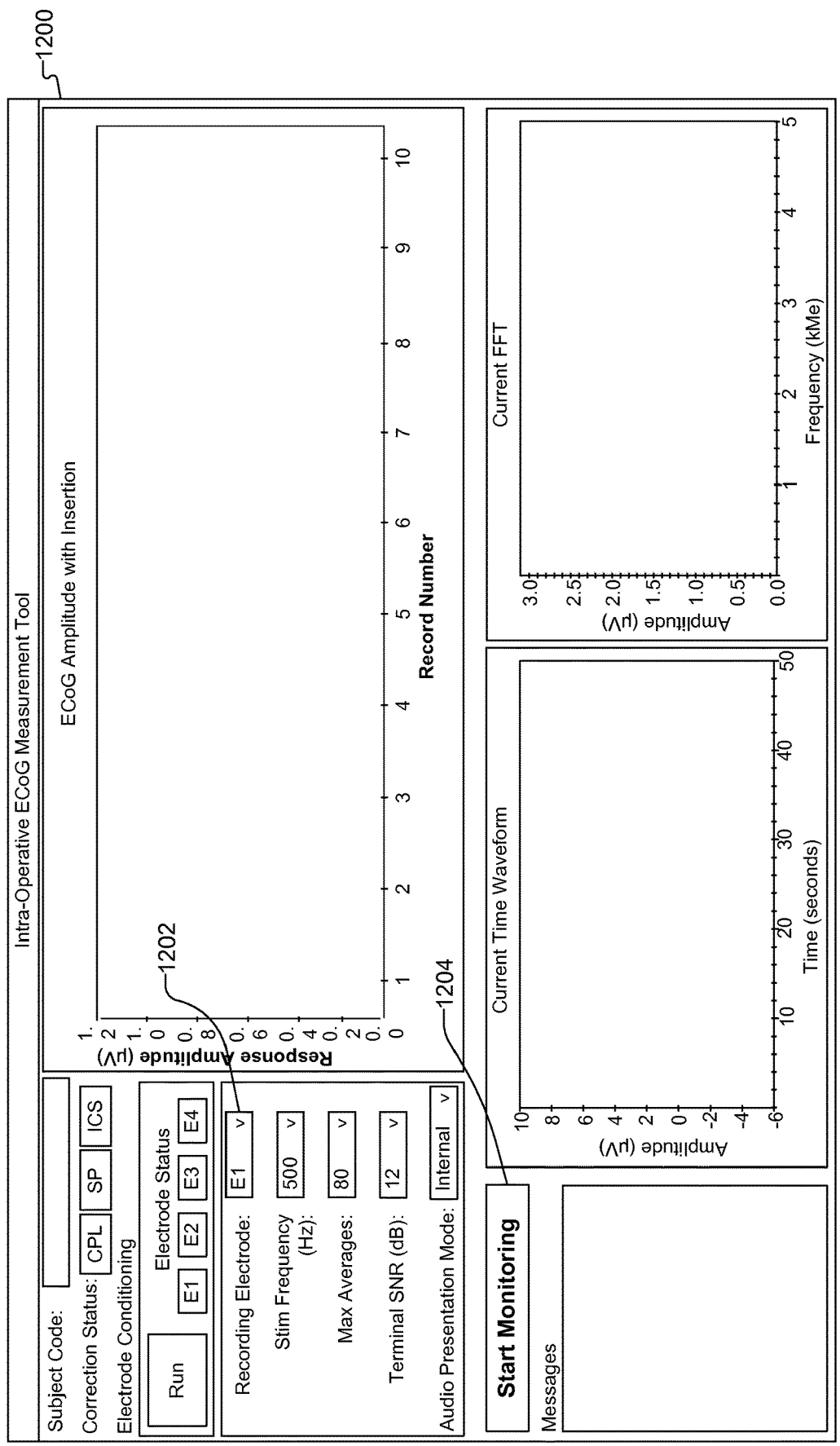
FIGS. 12-13 show exemplary graphical user interfaces according to principles described herein.

FIG. 12 shows an exemplary graphical user interface 1200 that may be presented by programming system 402 during an insertion procedure in which an electrode lead is inserted into a cochlea of a patient. As shown, graphical user interface 1200 includes an option 1202 (which, in this example, is a drop-down menu option) that allows a user to select which intracochlear electrode is to be shorted with the extracochlear electrode during the insertion procedure. In the particular example of FIG. 12, the user has selected an intracochlear electrode labeled "E1" to be shorted with the extracochlear electrode during the insertion procedure. The user may easily select a different intracochlear electrode for shorting by selecting, for example, the drop-down menu option 1202 and choosing a different intracochlear electrode. Graphical user interface 1200 may further include an option 1204 that may be selected by the user to provide the user input command for monitoring system 600 to begin monitoring for evoked responses.

Figure 13:
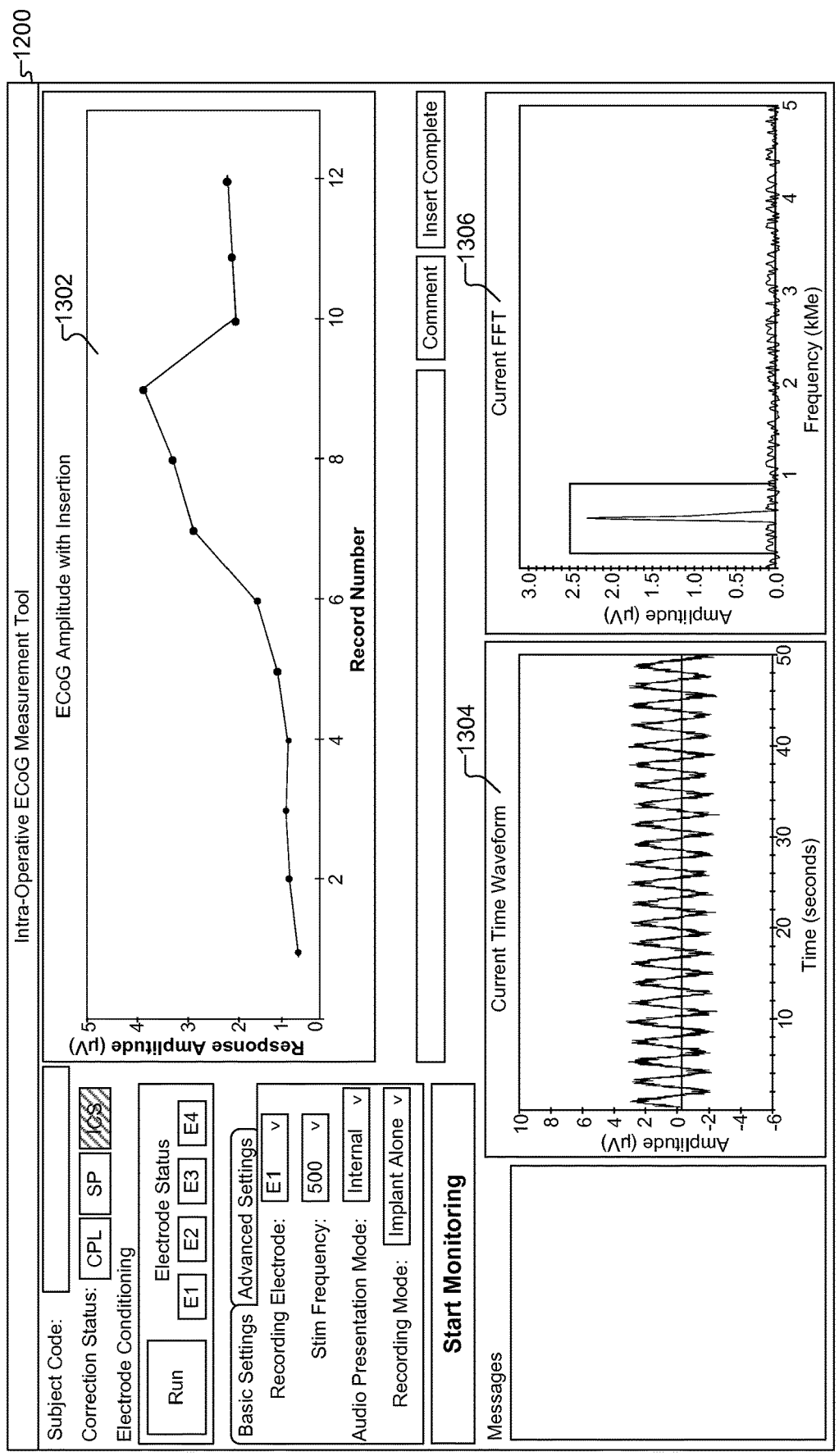

While monitoring system 600 monitors for evoked responses, programming system 402 may present, within graphical user interface 1200, graphical information associated with the evoked responses. For example, FIG. 13 shows that programming system 402 may present a graph 1302 that represents amplitudes of the evoked responses, a graph 1304 that represents a current time domain waveform of the evoked responses, and a graph 1306 that represents a current frequency domain waveform of the evoked responses. Additional or alternative graphical information associated with the evoked responses may be presented within graphical user interface 1200 as may serve a particular implementation.

In certain embodiments, one or more of the processes described herein may be implemented at least in part as instructions embodied in a non-transitory computer-readable medium and executable by one or more computing devices. In general, a processor (e.g., a microprocessor) receives instructions, from a non-transitory computer-readable medium, (e.g., a memory, etc.), and executes those instructions, thereby performing one or more processes, including one or more of the processes described herein. Such instructions may be stored and/or transmitted using any of a variety of known computer-readable media.

A computer-readable medium (also referred to as a processor-readable medium) includes any non-transitory medium that participates in providing data (e.g., instructions) that may be read by a computer (e.g., by a processor of a computer). Such a medium may take many forms, including, but not limited to, non-volatile media, and/or volatile media. Non-volatile media may include, for example, optical or magnetic disks and other persistent memory. Volatile media may include, for example, dynamic random access memory ("DRAM"), which typically constitutes a main memory. Common forms of computer-readable media include, for example, a disk, hard disk, magnetic tape, any other magnetic medium, a compact disc read-only memory ("CD-ROM"), a digital video disc ("DVD"), any other optical medium, random access memory ("RAM"), programmable read-only memory ("PROM"), erasable programmable read-only memory ("EPROM"), electrically erasable programmable read-only memory ("EEPROM"), a Flash EEPROM device, any other memory chip or cartridge, or any other tangible medium from which a computer can read.

Figure 14:
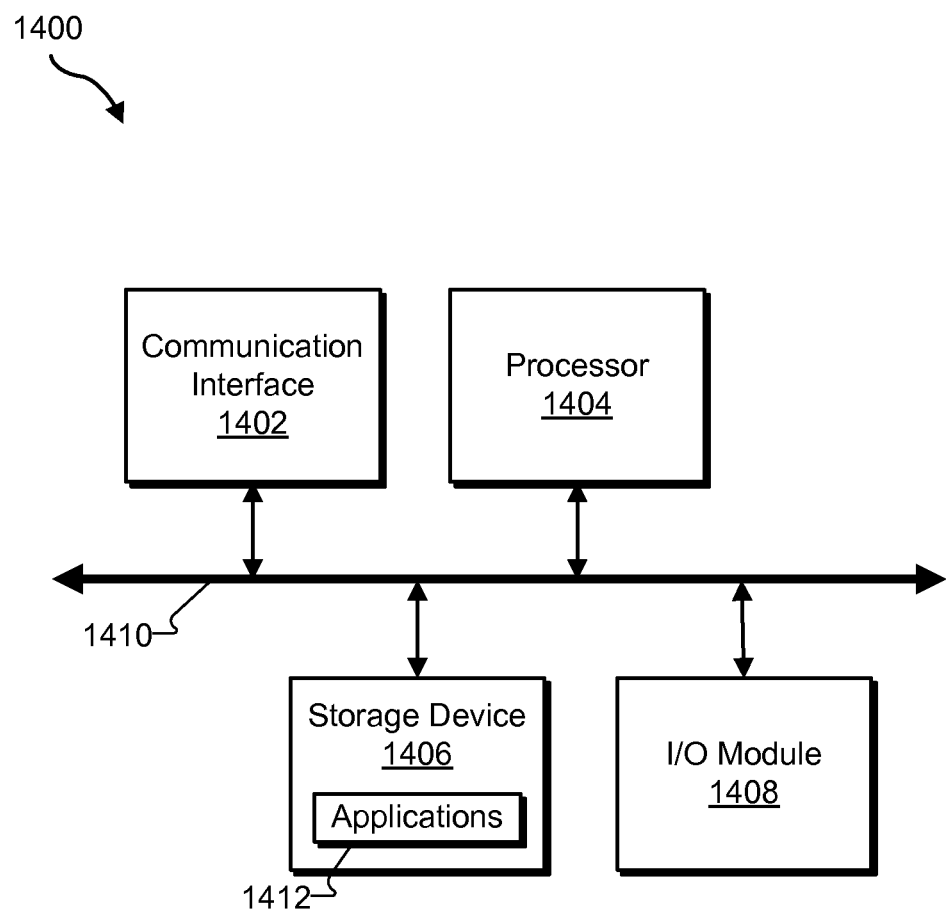
FIG. 14 illustrates an exemplary computing device according to principles described herein.

FIG. 14 illustrates an exemplary computing device 1400 that may be specifically configured to perform one or more of the processes described herein. As shown in FIG. 14, computing device 1400 may include a communication interface 1402, a processor 1404, a storage device 1406, and an input/output ("I/O") module 1408 communicatively connected via a communication infrastructure 1410. While an exemplary computing device 1400 is shown in FIG. 14, the components illustrated in FIG. 14 are not intended to be limiting. Additional or alternative components may be used in other embodiments. Components of computing device 1400 shown in FIG. 14 will now be described in additional detail.

Communication interface 1402 may be configured to communicate with one or more computing devices. Examples of communication interface 1402 include, without limitation, a wired network interface (such as a network interface card), a wireless network interface (such as a wireless network interface card), a modem, an audio/video connection, and any other suitable interface.

Processor 1404 generally represents any type or form of processing unit capable of processing data or interpreting, executing, and/or directing execution of one or more of the instructions, processes, and/or operations described herein. Processor 1404 may direct execution of operations in accordance with one or more applications 1412 or other computer-executable instructions such as may be stored in storage device 1406 or another computer-readable medium.

Storage device 1406 may include one or more data storage media, devices, or configurations and may employ any type, form, and combination of data storage media and/or device. For example, storage device 1406 may include, but is not limited to, a hard drive, network drive, flash drive, magnetic disc, optical disc, RAM, dynamic RAM, other non-volatile and/or volatile data storage units, or a combination or sub-combination thereof. Electronic data, including data described herein, may be temporarily and/or permanently stored in storage device 1406. For example, data representative of one or more executable applications 1412 configured to direct processor 1404 to perform any of the operations described herein may be stored within storage device 1406. In some examples, data may be arranged in one or more databases residing within storage device 1406.

I/O module 1408 may be configured to receive user input and provide user output and may include any hardware, firmware, software, or combination thereof supportive of input and output capabilities. For example, I/O module 1408 may include hardware and/or software for capturing user input, including, but not limited to, a keyboard or keypad, a touch screen component (e.g., touch screen display), a receiver (e.g., an RF or infrared receiver), and/or one or more input buttons.

I/O module 1408 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1408 is configured to provide graphical data to a display for presentation to a user. The graphical data may be representative of one or more graphical user interfaces and/or any other graphical content as may serve a particular implementation.

In some examples, any of the facilities or systems described herein may be implemented by or within one or more components of computing device 1400. For example, one or more applications 1412 residing within storage device 1406 may be configured to direct processor 1404 to perform one or more processes or functions associated with monitoring facility 602. Likewise, storage facility 604 may be implemented by or within storage device 1406.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:

1. A system comprising:
a sound processor included in an electro-acoustic stimulation ("EAS") system and physically and communicatively coupled to a loudspeaker, the sound processor configured to:
receive, from a programming system communicatively coupled to the sound processor, a user input command to begin monitoring evoked responses that occur in response to acoustic stimulation during an insertion procedure in which a lead that is communicatively coupled to a cochlear implant is inserted into a cochlea of a patient, the lead having an array of intracochlear electrodes disposed on a distal portion of the lead that are configured to be located within the cochlea when the insertion procedure is completed and an extracochlear electrode configured to be located external to the cochlea when the insertion procedure is completed, the extracochlear electrode physically and communicatively coupled to a probe that is also communicatively coupled to the sound processor,
transmit, in response to the user input command and by way of a wireless link, a command to the cochlear implant to short an intracochlear electrode included in the array of intracochlear electrodes with the extracochlear electrode,
present, while the intracochlear electrode is shorted with the extracochlear electrode, the acoustic stimulation to the patient by way of the loudspeaker, and
record the evoked responses that occur in response to the acoustic stimulation by using the intracochlear electrode to detect signals representative of the evoked responses, receiving the detected signals by way of the extracochlear electrode and the probe, and converting the detected signals from analog signals representative of the evoked responses into digital signals representative of the evoked responses.

2. The system of claim 1, wherein the sound processor is configured to convert the detected signals from the analog signals to the digital signals by using an analog-to-digital converter included in the sound processor and that is also used by the sound processor to convert analog audio signals detected by a microphone that is communicatively coupled to the sound processor into digital audio signals.

3. The system of claim 1, further comprising a programming system communicatively coupled to the sound processor, wherein the sound processor is configured to transmit data representative of the evoked responses to the programming system.

4. The system of claim 3, wherein the programming system is configured to:
present a graphical user interface during the insertion procedure;
transmit the user input command to the sound processor in response to a selection by a user of an option included in the graphical user interface;
display, within the graphical user interface based on the data representative of the evoked responses, graphical information associated with the evoked responses.

5. The system of claim 4, wherein the graphical information associated with the evoked responses comprises at least one of a graph that represents amplitudes of the evoked responses, a graph that represents a current time domain waveform of the evoked responses, or a graph that represents a current frequency domain waveform of the evoked responses.

6. The system of claim 4, wherein the programming system is further configured to present an option for the user to select which intracochlear electrode is to be shorted with the extracochlear electrode during the insertion procedure.

7. The system of claim 1, further comprising an amplifier that is physically and communicatively coupled to the probe and to the sound processor, wherein the amplifier is configured to:
receive the detected signals by way of the extracochlear electrode and the probe;
amplify the detected signals, wherein the amplification results in a plurality of amplified signals; and
transmit the amplified signals to the sound processor;
wherein the sound processor is configured to receive the detected signals by receiving the amplified signals.

8. The system of claim 1, wherein the extracochlear electrode comprises a ring electrode.

9. The system of claim 1, wherein the evoked responses comprise electrocochleography signals.

10. A system comprising:
a sound processor included in an electro-acoustic stimulation ("EAS") system; and
a programming system communicatively coupled to the sound processor and configured to:
receive a user input command to begin monitoring evoked responses that occur in response to acoustic stimulation during an insertion procedure in which a lead that is communicatively coupled to a cochlear implant is inserted into a cochlea of a patient, the lead having an array of intracochlear electrodes disposed on a distal portion of the lead that are configured to be located within the cochlea when the insertion procedure is completed and an extracochlear electrode configured to be located external to the cochlea when the insertion procedure is completed, the extracochlear electrode physically and communicatively coupled to a probe that is also communicatively coupled to the programming system,
transmit the user input command to the sound processor, wherein the sound processor is configured to direct, based on the user input command, the cochlear implant to short the intracochlear electrode with the extracochlear electrode by transmitting, in response to receiving the user input command from the programming system, a command to the cochlear implant by way of a wireless link that communicatively couples the sound processor and the cochlear implant, and
record the evoked responses that occur in response to acoustic stimulation that is applied to the patient during the insertion procedure by receiving, by way of the extracochlear electrode and the probe, signals representative of the evoked responses and converting the signals from analog signals representative of the evoked responses into digital signals representative of the evoked responses.

11. The system of claim 10, wherein the sound processor is configured to present the acoustic stimulation to the patient by way of a loudspeaker.

12. The system of claim 10, wherein the programming system is configured to present the acoustic stimulation to the patient by way of a loudspeaker.

13. The system of claim 10, further comprising an evoked potential machine communicatively coupled to the programming system and configured to present the acoustic stimulation to the patient by way of a loudspeaker.

14. The system of claim 10, further comprising an amplifier that is physically and communicatively coupled to the probe and to the programming system, wherein the amplifier is configured to:
receive the signals by way of the extracochlear electrode and the probe;
amplify the signals, wherein the amplification results in a plurality of amplified signals; and
transmit the amplified signals to the programming system;
wherein the programming system is configured to receive the signals by receiving the amplified signals.

15. The system of claim 10, wherein the extracochlear electrode comprises a ring electrode.

16. The system of claim 10, wherein the evoked responses comprise electrocochleography signals.

17. The system of claim 10, wherein the programming system is configured to:
present a graphical user interface during the insertion procedure;
receive the user input command in response to a selection by a user of an option included in the graphical user interface; and
display, within the graphical user interface, graphical information associated with the evoked responses.

18. The system of claim 17, wherein the graphical information associated with the evoked responses comprises at least one of a graph that represents amplitudes of the evoked responses, a graph that represents a current time domain waveform of the evoked responses, or a graph that represents a current frequency domain waveform of the evoked responses.

* * * * *